US007322936B2

(12) United States Patent
Takeuchi

(10) Patent No.: US 7,322,936 B2
(45) Date of Patent: Jan. 29, 2008

(54) ULTRASOUND DIAGNOSIS APPARATUS

(75) Inventor: Hideki Takeuchi, Mitaka (JP)

(73) Assignee: Aloka Co., Ltd., Tokyo (JP)

( * ) Notice: Subject to any disclaimer, the term of this patent is extended or adjusted under 35 U.S.C. 154(b) by 551 days.

(21) Appl. No.: 10/869,127

(22) Filed: Jun. 16, 2004

(65) Prior Publication Data

US 2004/0267126 A1    Dec. 30, 2004

(30) Foreign Application Priority Data

Jun. 25, 2003    (JP) .............................. 2003-181113

(51) Int. Cl.
*A61B 8/00* (2006.01)
(52) U.S. Cl. ...................................... 600/447; 128/916
(58) Field of Classification Search ........ 600/443–447, 600/455–456, 458; 128/916; 73/625–626
See application file for complete search history.

(56) References Cited

U.S. PATENT DOCUMENTS

| | | | |
|---|---|---|---|
| 5,229,933 A | | 7/1993 | Larson, III |
| 5,349,262 A | | 9/1994 | Grenon et al. |
| 5,563,346 A | | 10/1996 | Bartelt et al. |
| 5,617,862 A | | 4/1997 | Cole et al. |
| 5,832,923 A | | 11/1998 | Engeler et al. |
| 5,897,501 A | * | 4/1999 | Wildes et al. ............... 600/447 |
| 5,997,479 A | | 12/1999 | Savord et al. |
| 6,013,032 A | * | 1/2000 | Savord ......................... 600/443 |
| 6,089,096 A | * | 7/2000 | Alexandru .................... 73/626 |
| 6,102,863 A | | 8/2000 | Pflugrath et al. |
| 6,111,816 A | | 8/2000 | Chiang et al. |
| 6,120,449 A | * | 9/2000 | Snyder et al. ............... 600/447 |
| 6,174,286 B1 | * | 1/2001 | Ramamurthy et al. ....... 600/447 |
| 6,183,419 B1 | * | 2/2001 | Wildes ........................ 600/447 |
| 6,193,663 B1 | | 2/2001 | Napolitano et al. |
| 6,279,399 B1 | * | 8/2001 | Holm ........................... 73/626 |
| 6,375,617 B1 | * | 4/2002 | Fraser ......................... 600/443 |
| 6,419,633 B1 | * | 7/2002 | Robinson et al. ........... 600/443 |
| 6,491,634 B1 | | 12/2002 | Leavitt et al. |
| 6,524,254 B2 | * | 2/2003 | Erikson ....................... 600/447 |
| 6,537,219 B2 | | 3/2003 | Poland et al. |
| 6,537,220 B1 | * | 3/2003 | Friemel et al. ............. 600/447 |

(Continued)

FOREIGN PATENT DOCUMENTS

JP        9-322896        12/1997

(Continued)

*Primary Examiner*—Francis J. Jaworski
(74) *Attorney, Agent, or Firm*—William L. Androlia; H. Henry Koda

(57) ABSTRACT

In an ultrasound diagnosis apparatus, a plurality of sub arrays are defined on a 2D array transducer. The sub array shape pattern of each sub array is adaptively changed in accordance with the beam scanning direction. Each sub array is composed of a plurality of groups, each of which is composed of a plurality of transducer elements. With the change of sub array shape pattern in accordance with a beam scanning direction, the group shape pattern of each group also changes. The sub array shape changes for each sub array, and a variable region is determined by the largest outer edge of the shape changed. The variable regions partially overlap with each other among a plurality of sub arrays. On a 2D array transducer, a plurality of sub arrays are always closely coupled with each other even when each sub array shape is changed.

13 Claims, 12 Drawing Sheets

U.S. PATENT DOCUMENTS

| | | |
|---|---|---|
| 6,540,862 B1 | 4/2003 | Calvert et al. |
| 6,582,367 B1 | 6/2003 | Robinson et al. |
| 6,676,602 B1 * | 1/2004 | Barnes et al. ............... 600/443 |
| 6,868,729 B2 | 3/2005 | Amemiya |
| 7,090,642 B2 * | 8/2006 | Satoh ........................ 600/447 |
| 2003/0018260 A1 | 1/2003 | Erikson |
| 2005/0228277 A1 * | 10/2005 | Barnes et al. ............... 600/437 |
| 2005/0243812 A1 * | 11/2005 | Phelps ........................ 370/360 |

FOREIGN PATENT DOCUMENTS

| | | |
|---|---|---|
| JP | 10-267904 | 10/1998 |
| JP | 2000-254120 | 9/2000 |
| JP | 2000-300553 | 10/2000 |
| JP | 2001-104303 | 4/2001 |
| JP | 2001-276064 | 10/2001 |

* cited by examiner a, b, c : BELONGING TO R1, R2, AND R3
d, e, f : BELONGING TO R1, R2, AND R4
g, h, i : BELONGING TO R2, R3, AND R4
j, k, l : BELONGING TO R1, R3, AND R4

ULTRASOUND DIAGNOSIS APPARATUS

BACKGROUND OF THE INVENTION

1. Field of the Invention

The present invention relates to an ultrasound diagnosis apparatus for use in the field of medical treatment, and more particularly to setting of a plurality of sub arrays on an array transducer.

2. Description of Related Art

Ultrasound diagnosis apparatuses are used in the field of medical treatment for the purpose of diagnosing diseases of a living body (patient). More specifically, ultrasonic diagnosis apparatuses transmit an ultrasonic pulse to a living body and receive a reflected wave therefrom for forming an ultrasonic image based on a receiving signal obtained by the reflected wave received.

A two-dimensional (2D) array transducer (or transducer array) is used for effecting two-dimensional scanning of ultrasonic beams to thereby form a three-dimensional echo data acquiring space within a living body. A 2D transducer is generally composed of a plurality of transducer elements arranged along X and Y directions.

In some 2D array transducers, a plurality of sub arrays are defined on the 2D array transducer for the purpose of channel reduction of a transmission/reception section, simultaneous formation of a plurality of receiving beams, or other purposes. Conventionally, a plurality of sub arrays are fixedly defined on the 2D array transducer. For example, a plurality of sub arrays having a rectangular shape are set with respect to a 2D array transducer, and in this case, the shape of each sub array cannot be changed. Japanese Patent Laid-Open Publication No. 2001-276064 discloses the grouping of a plurality of transducer elements in which the structure of each group is fixed. Japanese Patent Laid-Open Publication No. 2001-104303 discloses a structure for performing phase adjustment and summation (or beam formation) in two stages. Japanese Patent Laid-Open Publication No. Hei 9-322896 discloses, in FIG. 6, that a plurality of groups are fixedly set for a 2D array transducer, that a plurality of first beam formers are connected to the plurality of groups, and that a plurality of second beam formers are provided at the subsequent stage of the plurality of first beam formers. U.S. Pat. No. 5,832,923 discloses that a plurality of 2D sub arrays are defined on a 2D array transducer and that a plurality of groups are defined on each sub array. None of these documents, however, describes dynamically changing the shape of each sub array.

When the structure or form of the sub array is fixedly defined, a problem results in that a beam profile preferable to specific transmitting and receiving wave conditions cannot be obtained. For example, there may be a tendency for side lobes to be generated in a specific beam scanning direction.

SUMMARY OF THE INVENTION

The present invention advantageously provides an ultrasound diagnosis apparatus capable of providing an excellent beam profile.

The present invention advantageously enables the maintenance or improvement of image quality of an ultrasonic image when channel reduction of a transmission/reception section is performed.

(1) An ultrasound diagnosis apparatus in accordance with one aspect of the present invention comprises (a) an array transducer having a plurality of transducer elements arranged two-dimensionally, (b) a switching section for defining a plurality of sub arrays with respect to the plurality of transducer elements, and (c) a receiving processing section for processing a plurality of receiving signals output from the array transducer, wherein (d) the switching section changes a sub array shape pattern of at least one sub array in the array transducer.

With the above structure, the switching section defines a plurality of sub arrays on the array transducer. Because the switching section has a function of changing the sub array shape pattern of the sub array, a conventional problem caused by fixedly defining the sub array shape pattern can be solved or improved. For example, due to the change of sub array shape pattern, a beam profile is changed to an excellent beam profile, whereby side lobes can be reduced.

Preferably, the switching section changes the sub array shape pattern of each of a plurality of sub arrays. A plurality of sub arrays are preferably coupled with each other closely on the array transducer according to their acoustic power or sensitivity. In other words, it is desirable that all the transducer elements forming the array transducer belong to one sub array. However, an interval may be formed between sub arrays. In other words, there may be transducer elements which do not belong to any sub array and do not function in transmission and reception. Further, when a certain sub array shape pattern is selected, a plurality of transducer elements which do not function in transmitting and receiving may be provided around the array transducer.

Preferably, an identical sub array shape pattern is defined for a plurality of sub arrays. This structure facilitates close coupling of a plurality of sub arrays with respect to each other. It is of course possible to individually define the sub array shape pattern for each sub array.

Preferably, a control section for switching the sub array shape pattern in accordance with a beam forming condition is further provided. Preferably, the array transducer is a 2D array transducer in which a plurality of transducer elements are arranged in the X and Y directions, and the beam forming condition includes a beam scanning direction on a X-Y plane. The beam forming condition may further include a beam deflecting angle, a beam width, a beam shape, and the like.

Preferably, the switching section further establishes a plurality of groups for each of the sub arrays, each of the plurality of groups being composed of a plurality of transducer elements, the receiving processing section processes a group receiving signal output from each of the groups within each sub array, and the switching section further has a function of changing a group shape pattern of each group with a change of the sub array shape pattern.

With this structure, the switching section performs sub array setting and group setting, and a desired sub array shape pattern and a desired group shape pattern can therefore be established.

For example, when n groups are set with respect to m transducer elements forming a certain sub array (1<n<m), a channel reduction ratio of n/m is achieved. By performing such a channel reduction process within the probe head, the advantage of reducing the number of signal lines inserted through the probe cable can be obtained. With such grouping, a plurality of receiving signals are summed and combined into a single receiving signal (a group receiving signal). Further, a single transmitting signal can be supplied in parallel to a plurality of transducer elements forming one group.

Preferably, the number of transducer elements forming each group is variable in accordance with a beam forming condition. Preferably, the beam forming condition includes a beam scanning direction. Preferably, one or a plurality of ineffective transducer elements are included in each sub array in accordance with a beam forming condition. Here, the ineffective transducer element refers to a transducer element which is not used in transmission and reception of ultrasonic waves. Within a sub array, a plurality of transducer elements other than one or a plurality of ineffective transducer elements are effective transducer elements, and these effective transducer elements are divided into a plurality of groups.

Each of a plurality of groups which are set for each sub array may be composed of the same number of transducer elements. With this structure, the number of receiving signals to be summed can be identical among the plurality of groups, and the number of branches (the number of destinations) for a transmitting signal can also be identical among the plurality of groups.

Further, the same group shape pattern may be set for a plurality of groups. In this case, a group shape pattern which forms substantially a straight line may be set for each group. It is desirable that each group is defined so as to have a linear shape which crosses the beam scanning direction (which is preferably orthogonal to the beam scanning direction), or is formed into a string shape having a small width in that direction.

Preferably, a control section for switching the group shape pattern along with the sub array shape pattern in accordance with a beam forming condition is further provided. Preferably, the plurality of sub arrays are closely coupled with each other even when the sub array shape pattern is changed. When a plurality of sub arrays are closely coupled with each other, it is possible to operate a great number of available transducer elements, thereby increasing acoustic power.

Preferably, on the array transducer, a pattern variable region is defined for each sub array, whereby a plurality of pattern variable regions are defined on the array transducer, the pattern variable region for each sub array corresponds to a region formed by combining a plurality of sub array shape patterns concerning each sub array, and the plurality of pattern variable regions partially overlap with each other. Preferably, each pattern variable region covers a plurality of transducer elements peculiar to each sub array and a plurality of transducer elements existing on a portion where the plurality of pattern variable regions partially overlap.

(2) An ultrasound diagnosis apparatus in accordance with another aspect of the present invention comprises (a) an array transducer having a plurality of transducer elements, (b) a switching section for defining a plurality of sub arrays with respect to the plurality of transducer elements and for setting a plurality of groups for each sub array and outputting a group receiving signal for each of the groups, (c) a receiving processing section for processing a plurality of group receiving signals output from the switching section, and (d) a control section for controlling the switching section in accordance with a beam scanning condition, wherein (e) the control section controls an operation of the switching section to change a sub array shape pattern of each sub array and change a group shape pattern of each group.

Preferably, the receiving processing section includes a plurality of sub phase adjusting and summing circuits, each sub phase adjusting and summing circuit performing a sub phase adjusting and summing process with respect to a plurality of group receiving signals output from each sub array and outputting a sub phase adjusted and summed signal, and a main phase adjusting and summing circuit for performing a main phase adjusting and summing process with respect to a plurality of sub phase adjusted and summed signals output from the plurality of sub phase adjusting and summing circuits.

With the above structure, after the sub phase adjusting and summing process is performed for each group, the main phase adjusting and summing process is applied to a plurality of sub phase adjusted and summed signals. A plurality of main phase adjusting and summing circuits may be disposed in parallel for simultaneously forming a plurality of receiving beams by one receiving process. Further, in the probe cable, a transmitting signal may be transmitted in the form of a voltage signal and a receiving signal may be transmitted in the form of a current signal. The transmitting signal may be an approximately 100V voltage signal, or may be a low voltage signal of several to ten-odd V. In the latter case, it is desirable that each transducer element is formed in a laminate structure, for example, so that electrical impedance of each transducer element is reduced.

Preferably, at least the array transducer and the switching section are provided within the probe head. Further, a plurality of sub phase adjusting and summing circuits may be provided within the probe head (in this case, the number of signal lines can be further reduced), or a plurality of sub phase adjusting and summing circuits may be provided within the probe connector or the apparatus body. The transmitter section can be provided in the probe head, the cable connector, or the apparatus body.

(3) An ultrasound diagnosis apparatus in accordance with a further aspect of the present invention comprises (a) an array transducer having a plurality of transducer elements, (b) a switching section for setting a plurality of sub arrays with respect to the plurality of transducer elements, and (c) a control section for controlling the switching section to adaptively change a sub array shape pattern of each of the sub arrays in accordance with a beam scanning direction.

Preferably, each sub array shape pattern is formed by a plurality of pattern elements, and each of the plurality of pattern elements is formed by a series of transducer elements arranged in a substantially linear shape. Preferably, each series of transducer elements is substantially orthogonal with respect to the beam scanning direction. Preferably, each sub array has a quadrangle shape when the beam scanning direction is 0 degrees, 90 degrees, 180 degrees, and 270 degrees, and the shape of each sub array is changed from the quadrangle shape to a parallelogram or the like when the beam scanning direction is an angle other than the noted angles. Even when each sub array has a parallelogram shape or other shapes, it is desirable that a plurality of sub arrays are closely coupled with each other.

Preferably, the control section sets one or a plurality of ineffective transducer elements within each sub array in accordance with the beam scanning direction, and also defines a plurality of groups by means of a plurality of effective transducer elements other than the one or a plurality of ineffective transducer elements within each sub array. Preferably, the control section defines a plurality of groups within each sub array in accordance with the beam scanning direction, and the control section changes a group shape pattern of each of the groups in accordance with the beam scanning direction and also changes the number of transducer elements forming each group in accordance with the beam scanning direction.

BRIEF DESCRIPTION OF THE DRAWINGS

These and other objects of the invention will be explained in the description below, in connection with the accompanying drawings, in which.

DESCRIPTION OF PREFERRED EMBODIMENTS

Preferred embodiments of the present invention will be described with reference to the drawings.

Figure 10:
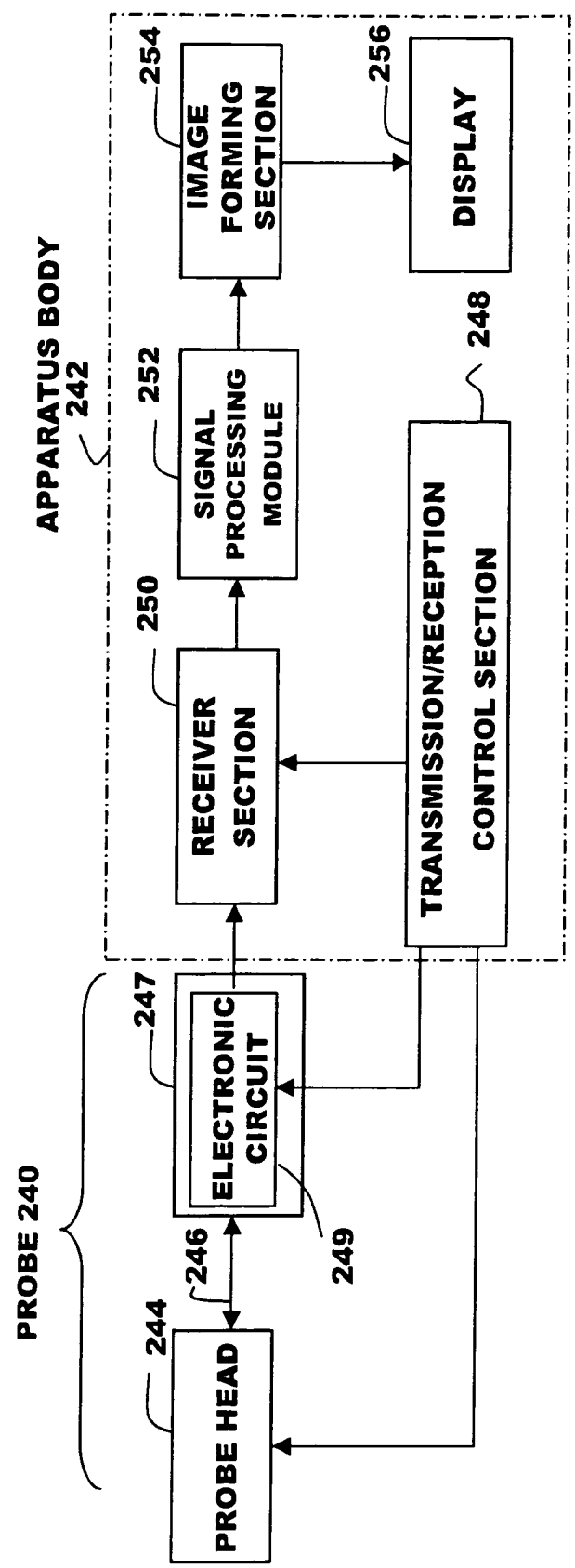
FIG. 10 is a block diagram showing a whole structure of an ultrasound diagnosis apparatus in accordance with an embodiment of the present invention.

Referring first to FIG. 10, a basic structure of an ultrasound diagnosis apparatus according to a first embodiment of the present invention will be described. The ultrasound diagnosis apparatus is composed of a probe (probe unit) 240 and an apparatus body 242. The probe 240 includes a probe head 244, a probe cable 246, and a cable connector 247. The apparatus body 242 includes a transmission/reception control section 248, a receiver section 250, a signal processing module 252, an image forming section 254, and a display 256. The cable connector 247 is detachably connected to a connector (not shown) of the apparatus body 242. In the present embodiment, the cable connector 247 includes a built-in electronic circuit 249, which performs a sub phase adjusting and summing process and a transmitting signal generating process, as will be further described below with reference to FIGS. 1 and 2. The probe head 244 transmits and receives ultrasound. A receiving signal, which is obtained by transmission and reception of ultrasound, is then input to the image forming section 254 through the electronic circuit 249, the receiver section 250 and the signal processing module 252. The image forming section 254 forms an ultrasonic image based on the signal received. The ultrasonic image is displayed on the screen of the display 256. Two-dimensional tomography images, two-dimensional blood stream images, three-dimensional images are known as ultrasonic images. In the present embodiment, volume data obtained from a three-dimensional space within a living body is subjected to a volume rendering process to form a three-dimensional image. Many other methods for forming a three-dimensional image are also known, and may be applied when preferable.

Figure 1:
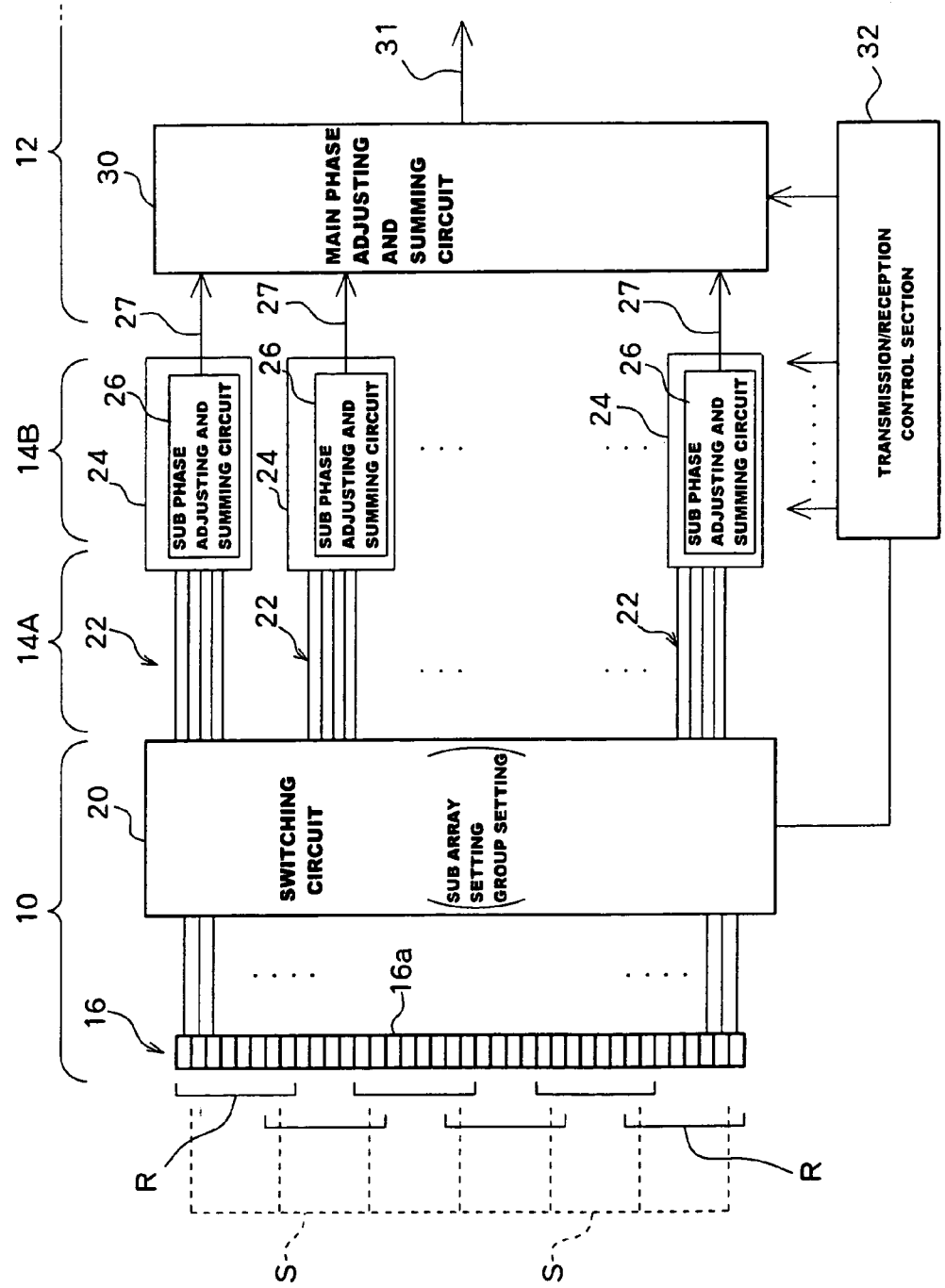
FIG. 1 a block diagram showing a transceiver section in an ultrasound diagnosis apparatus according to the present invention.

FIG. 1 is a block diagram showing a structure of a transmitter/receiver(transceiver) section in an ultrasound diagnosis apparatus according to the embodiment. The ultrasound diagnosis apparatus as shown is composed of a probe unit and an apparatus body 12. The probe unit is composed of a probe head 10, a probe cable 14A, and a cable connector 14B.

In this embodiment, a plurality of transmission/reception modules 24 (corresponding to the electronic circuit 249 described above), which will be described below, are included within the cable connector 14B. However, the plurality of transmission/reception modules 24 may be provided within the probe head 10 or within the apparatus body 12.

The probe head 10, which is used in contact with a body surface, for example, is a wave transmitter/receiver for effecting transmission and reception of ultrasound. The probe head includes a 2D array transducer 16 which forms an ultrasonic beam. The ultrasonic beam is two-dimensionally scanned electronically, thereby forming a three-dimensional echo data acquiring space (a three-dimensional space). The electronic scanning method of ultrasonic beam includes electronic sector scanning, for example.

In the present embodiment, the array transducer 16 is composed of a great number of (3000 or 4000, for example) transducer elements 16a which are arranged two-dimensionally, as will be described below with reference to FIG. 3.

The switching circuit 20 is formed in the form of a multiplexer or a switching matrix. In the present embodiment, the switching circuit 20 has a function of defining a plurality of sub arrays on the 2D array transducer 16 and a function of setting a plurality of groups for each sub array. The switching circuit 20 also has a function of changing a shape of each sub array (a sub array shape pattern) and a function of changing a shape of each group (a group shape pattern). The switching circuit 20 may be formed by a single circuit as shown in FIG. 1 or by a plurality of circuits.

In FIG. 1, a plurality of sub arrays S which are defined by the switching circuit 20 are conceptually shown. A plurality of sub arrays S are closely coupled with each other on the 2D array transducer 16, and all the transducer elements 16a are basically used to form the plurality of sub arrays S. In the present embodiment, the sub array shape pattern for each sub array can be changed as described above, and the pattern variable region for each sub array is conceptually shown and indicated by R in FIG. 1. The sub array shape pattern and a changing method thereof will be described in detail below. A plurality of groups are set for each sub array. Each group shape pattern changes with the change of sub array shape pattern. However, in the present embodiment, the number of transducer elements forming each group is fixed and invariable. Of course, the number of transducer elements forming each group may be individually set variably. Here, it is possible to set the sub array shape pattern for each sub array individually.

In the present embodiment, each sub array is composed of 5×5=25 transducer elements, which are grouped or divided into 5 groups each including 5 transducer elements. In other words, a channel reduction ratio of 1/5 is achieved within the probe head 10.

The number of terminals in the switching circuit 20 is the same as the number of transducer elements forming the 2D array transducer 16 on the side of 2D array transducer 16, and the number of series of terminals is the same as the number of sub arrays on the side of apparatus body 12. In the example shown in FIG. 1, each series of terminals provided on the side of the apparatus body 12 is composed of 5 terminals (that is, the same number of terminals as the number of groups set on a single sub array). More specifically, the switching circuit 20 selectively connects an array of element signal lines with an array of group signal lines. The array of group signal lines is composed of a plurality of sets of group signal lines 22, and in the example shown in FIG. 1, each set of group signal lines is composed of 5 group signal lines. The switching circuit 20 includes a plurality of switches (not shown) respectively provided at intersections between the array of element signal lines and the array of group signal lines. With the ON/OFF operation of each of these switches, one or a plurality of transducer elements to be connected with each group signal line are selected. The switching circuit 20 is capable of varying the number of transducer elements forming each group in accordance with the beam scanning direction (namely, the beam deflecting direction). The switching circuit 20 is also capable of setting one or a plurality of ineffective transducer elements (i.e., a transducer element which is not connected with any group signal line and does not effect transmission and reception of ultrasound) in accordance with the beam scanning direction. Further, it is also possible that each sub array is composed of 4×4=16 transducer elements, for example, which are grouped into 4 groups. Still further, the sub array and the group may be defined under other conditions.

As can be understood from the above description, the switching circuit 20 outputs 5 group receiving signals for each sub array. Each group receiving signal is obtained by summing 5 receiving signals output from 5 transducer elements forming each group. In the example used to illustrate this embodiment, the summing is achieved by a simple summing method using connection. In other words, 5 receiving signals are summed by interconnection of 5 signal lines. However, a weighted addition method or the like may be employed. On the other hand, as will be described below, 5 transmitting signals are generated for each sub array within the cable connector 14B, and these 5 transmitting signals are supplied to 5 groups forming the corresponding sub array, respectively. Specifically, one transmitting signal is supplied in parallel to 5 transducer elements forming one group. Namely, within the switching circuit 20, one transmitting signal is divided into 5 signals.

As described above, numeral 22 indicates sets of signal liens provided for each sub array. Each set of signal lines 22 is composed of 5 signal lines (5 group signal lines). The above-described transmitting signal and the receiving signal are transmitted to each signal line. Here, it is possible for the receiving signal to be transmitted in the form of a current signal and that the transmitting signal is transmitted in the form of a voltage signal. In this case, the transmitting signal may be an approximately 100V voltage signal, for example, or a low voltage signal of approximately several V. The probe cable 14A also includes, in addition to the plurality of sets of signal lines 22, one or a plurality of control lines for transmitting a control signal or the like. In FIG. 1, a power line or the like inserted through the probe cable 14A is omitted.

The cable connector 14B has a box shape, for example, and a plurality of transmission/reception modules 24 are contained therein as described above. Each transmission/reception module 24 includes a transmitter section and sub phase adjusting and summing circuits (or beam formers) 26. The transmitter section includes 5 transmitters, thereby generating 5 transmitting signals for each sub array. Further, the sub phase adjusting and summing circuit 26 performs a sub phase adjusting and summing process with respect to 5 group receiving signals which are input thereto. With this process, a sub phase adjusted and summed signal 27 is generated for each sub array.

In the present embodiment, a main phase adjusting and summing circuit (or a main beam former) 30 and a transmission/reception control section 32 are provided within the apparatus body 12. The main phase adjusting and summing circuit 30 receives a plurality of sub phase adjusted and summed signals 27 and performs a main phase adjusting and summing process to these signals, thereby generating a main phase adjusted and summed signal (a receiving beam signal) 31. A known technology for dynamic focus in receiving can be applied to the phase adjusting and summing process. Each of the sub phase adjusting and summing circuits 26 and the main phase adjusting and summing circuit 30 may be formed as an analog phase adjusting and summing circuit or as a digital phase adjusting and summing circuit.

The transmission/reception control section 32 performs an operation control for each of the elements shown in FIG. 1, in particular, setting of a phase adjusting and summing condition in a plurality of sub phase adjusting and summing circuits 26 and setting of phase adjusting and summing conditions in the main sub phase adjusting and summing circuits 30. Further, the transmission/reception control section 32 outputs a control signal to the switching circuit 20 provided within the probe head 10. With this control signal, setting of a plurality of sub arrays and setting of a plurality of groups is performed.

Figure 2:
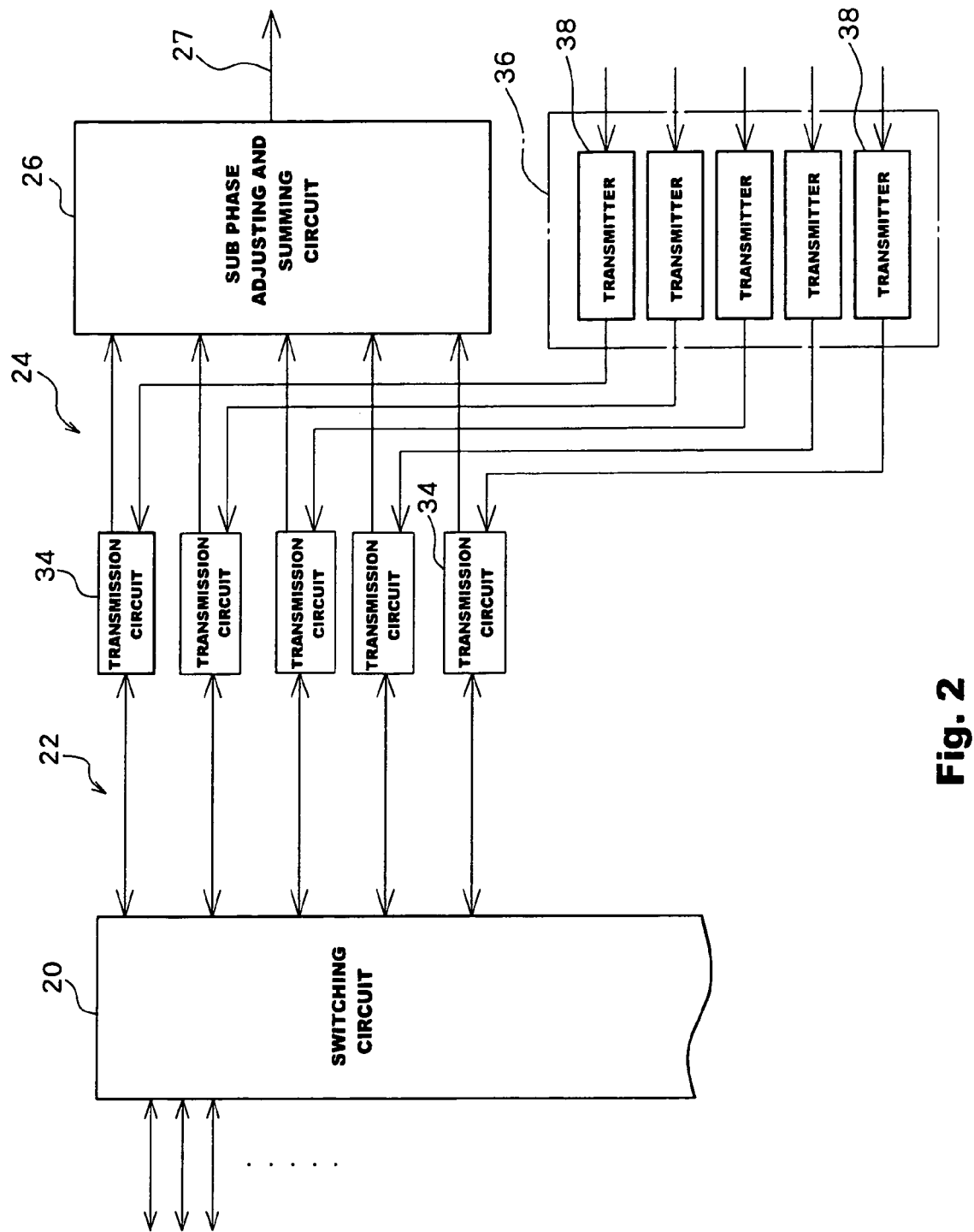
FIG. 2 is a block diagram showing a specific example structure of the transmission/reception module shown in FIG. 1.

FIG. 2 shows a specific example structure of the transmission/reception module 24 shown in FIG. 1. As described above, the transmission/reception module 24 includes the transmitter section 36, the sub phase adjusting and summing circuit 26, and a plurality of two-way transmission circuits (input-output circuits) 34. Here, each two-way transmission circuit 34 functions as a pulser for transmitting and a head amp circuit for receiving. Each two-way transmission circuit 34 outputs a transmitting signal to a signal line at the time of transmitting and transmits a receiving signal input from a signal line to the phase adjusting and summing circuit 26 at the time of receiving. The transmitter section 36 is composed of 5 transmitters 38. Each transmitter 38 outputs a transmitting signal to which a predetermined delay time is added.

The sub phase adjusting and summing circuit 26 described above may be formed as an analog phase adjusting and summing circuit having a delay line, for example, or may be formed in the form of a digital phase adjusting and summing circuit functioning as a digital beam former. Further, the sub phase adjusting and summing circuit 26 may also be formed as a phase adjusting and summing circuit using a CCD device.

A variety of embodiments can be employed for the elements provided on the apparatus body side with respect to the switching circuit 20, and the structure shown in FIG. 1 is one of the examples.

The operation of the switching circuit 20 will be described with reference to FIGS. 3 to 9.

Figure 3:
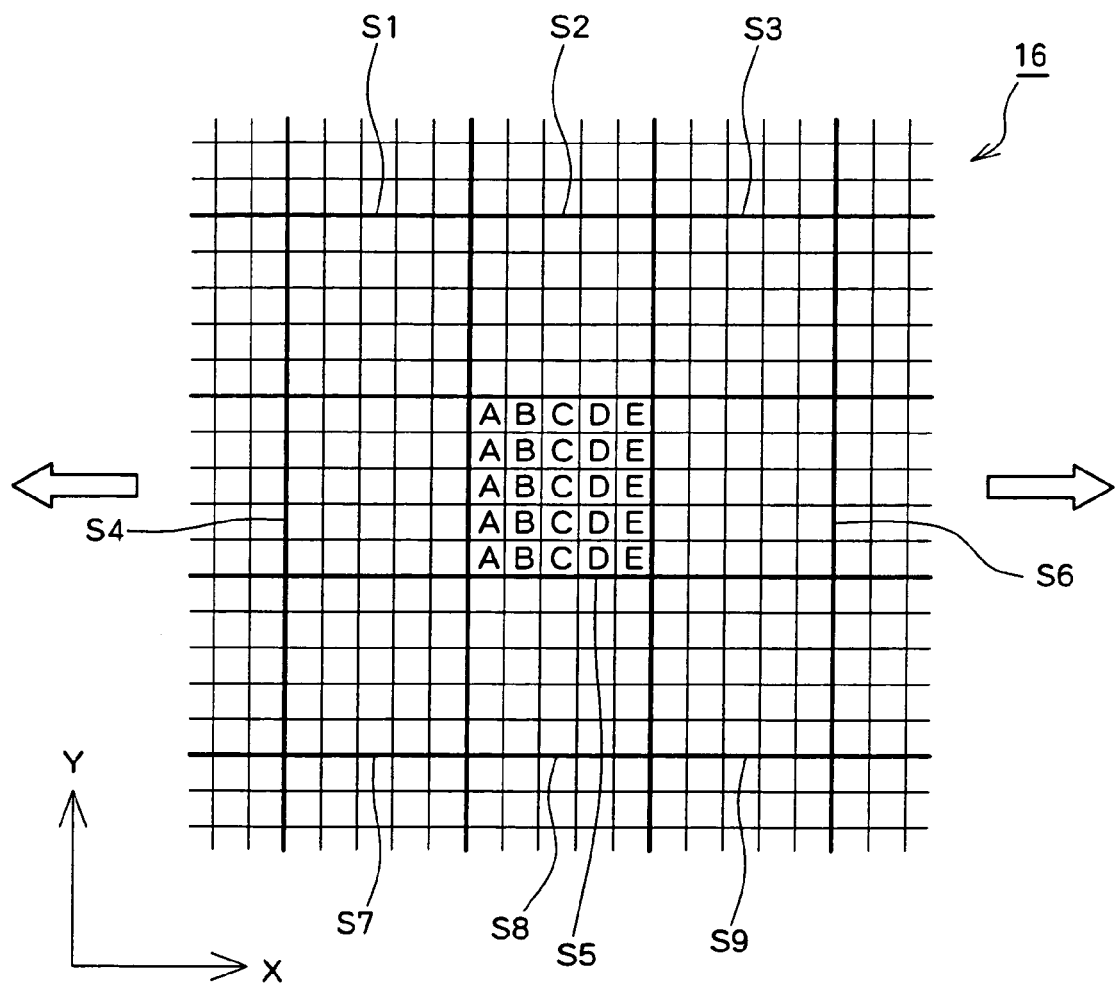
FIG. 3 is a view showing an example sub array shape pattern.

FIG. 3 conceptually shows a portion of the 2D array transducer 16. Each cell corresponds to one transducer element. A plurality of sub arrays having a rectangular sub array shape pattern are defined on the 2D array transducer 16. FIG. 3 particularly shows sub arrays S1 to S9, which are closely coupled with each other with no interval therebetween. In FIG. 3, an example group setting method is shown, for reference, with regard to the sub array S5. In the example shown in FIG. 3, 5 groups are set in the X direction, and each group is composed of 5 transducer elements arranged along the Y direction. In FIG. 3, A, B, C, D, or E is an identifier of the group to which each transducer element belongs. This similarly applies to each of the drawings which will be described below.

The sub array shape pattern shown in FIG. 3 is the most common sub array shape pattern, which is a square. The group shape pattern of each group shown in FIG. 3, which is a linear shape extending in the Y direction, is also common. This grouping pattern (the arrangement of a plurality of groups within the sub array) is adopted when an ultrasonic beam is scanned in the X direction as shown in FIG. 3, for example.

Figure 4:
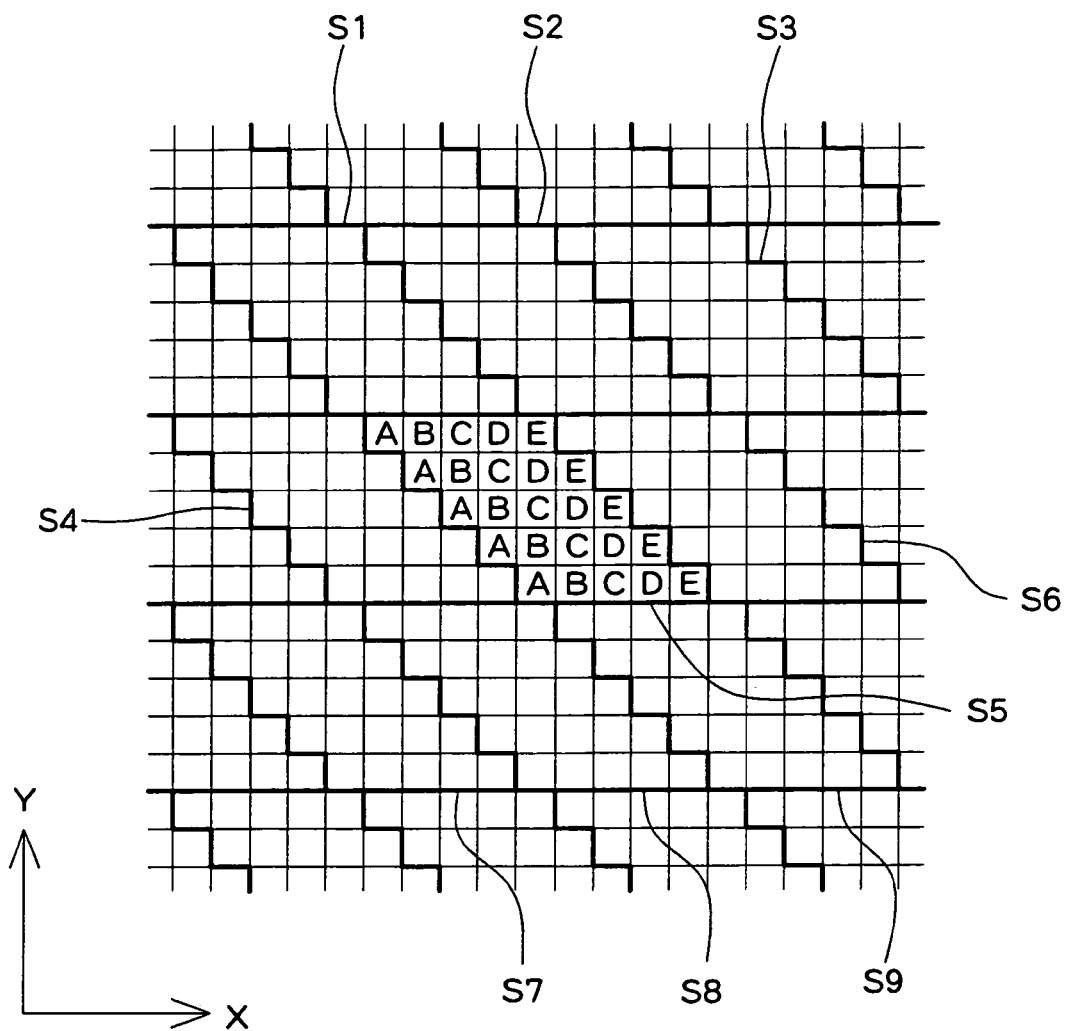
FIG. 4 is a view showing another example sub array shape pattern.

FIG. 4 shows another example of the sub array shape pattern. Each sub array S1 to S9 is slanted stepwise in the diagonal direction and has a parallelogram shape as a whole. When focusing an attention to the sub array S5, for example, the grouping as shown is achieved. Specifically, a group A is composed of 5 transducer elements which are linearly aligned diagonally. Although all of the other groups have the same structure, the position in the X direction for each group is shifted in parallel by one step at each stage in the Y direction stepwise. For other sub arrays, the completely identical grouping pattern with that of the sub array S5 is used.

By adopting the sub array shape pattern and the group shape pattern as shown in FIG. 4, when an ultrasonic beam is scanned in the direction which is slanted by 45 degrees with respect to the both X and Y directions, the thickness of each group in that direction can be reduced to that corresponding to one transducer element, namely it is possible to prevent a problem that the width of the transducer portion increases apparently in the beam scanning direction. This will be described in detail. In the present embodiment, the same delay time is added on group units. In other words, a plurality of transducer elements forming each group are connected in parallel at the time of transmitting and receiving, and they form a single transducer portion as a whole. When the width of such a transducer portion increases in the beam scanning direction, side lobes levels might be increased. On the other hand, when the sub array shape pattern and the group shape pattern are appropriately defined as shown in FIG. 4, it is possible to prevent the width of the transducer portion from being apparently increased. In other words, the above-noted problems can be solved or mitigated.

Figure 5:
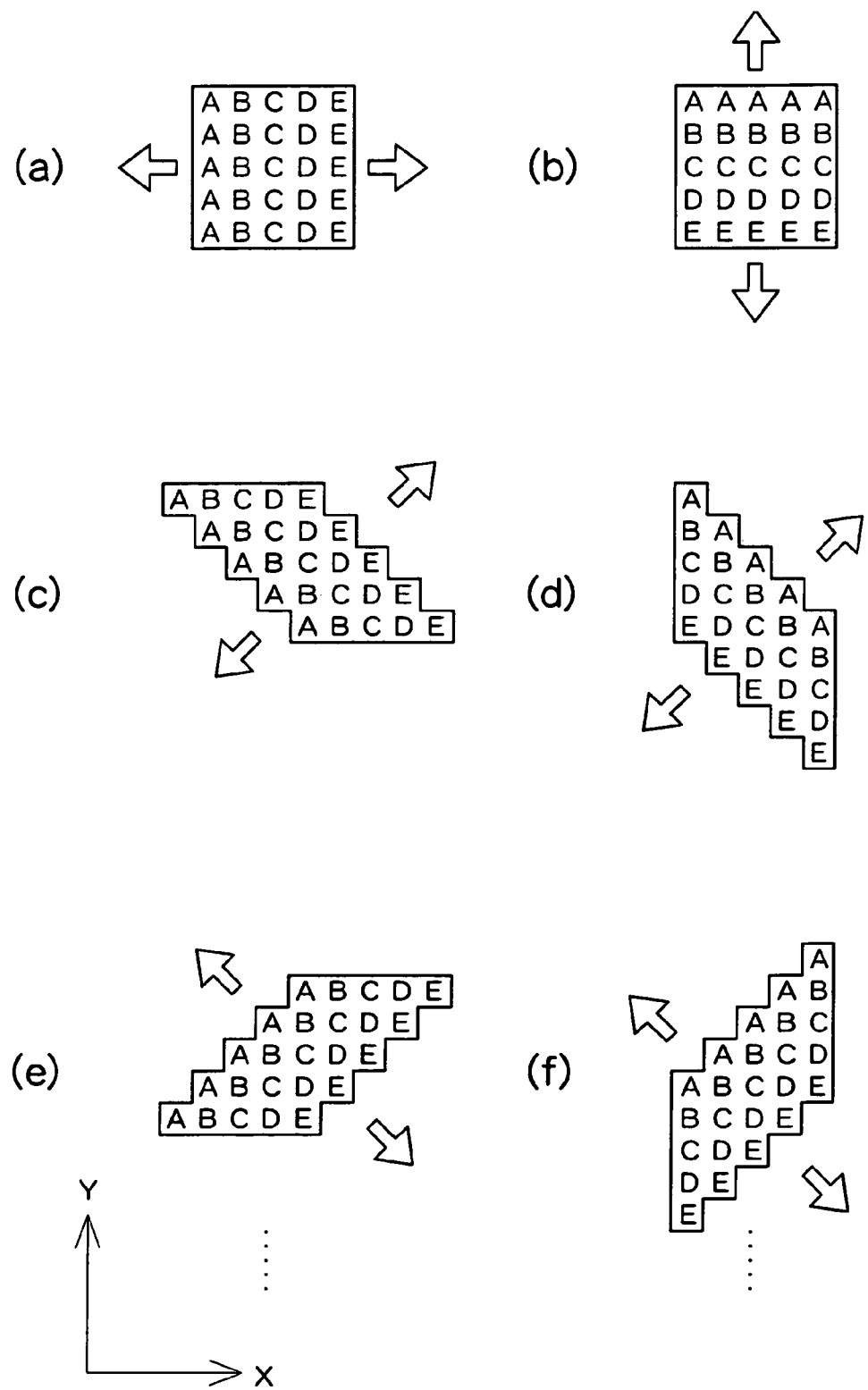
FIG. 5 is a view for explaining a plurality of sub array shape patterns in comparison.

FIG. 5 shows various types of sub array patterns and grouping patterns. The sub array shape pattern shown in FIG. 5(a) is the same as that shown in FIG. 3 and is used when scanning an ultrasonic beam in the X direction. The sub array shape pattern shown in FIG. 5(b) is the same as that shown in FIG. 5(a) with respect to the outer shape, but has a different grouping pattern within the sub array. More specifically, in FIG. 5(b), 5 groups are arranged in the Y direction, and each group is composed of 5 transducer elements arranged in the X direction. This pattern is adopted when scanning an ultrasonic beam in the Y direction.

FIG. 5(c) shows a sub array shape pattern which is the same as that shown in FIG. 4. The sub array shape pattern shown in FIG. 5(d) is obtained by shifting the sub array shape pattern shown in FIG. 5(b) stepwise in the X direction by one step at each stage in the Y direction. The sub array shape pattern shown in FIG. 5(d), as well as that shown in FIG. 5(c), is preferable when scanning an ultrasonic beam upwardly to the right (downward and to the left) with respect to the sheet surface.

The sub array shape pattern shown in FIG. 5(e) has a shape obtained by deforming the sub array shape pattern shown in FIG. 5(c) in the opposite diagonal direction. This sub array shape pattern is preferable when scanning an ultrasonic beam upward and to the left (downward and to the right) with respect to the sheet surface.

The sub array shape pattern shown in FIG. 5(f) has a shape obtained by deforming the sub array shape pattern shown in FIG. 5(d) in the opposite diagonal direction. This sub array shape pattern, similar to that shown in FIG. 5(e), is preferable when scanning an ultrasonic beam upward and to the left (downward and to the right) with respect to the sheet surface.

Obviously, these sub array shape patterns or the like shown in FIG. 5 are illustrative only, and a variety of other sub array shape patterns can also be adopted. Specifically, it is desirable to set the sub array shape pattern and the grouping pattern in accordance with transmitting and receiving condition, particularly the beam scanning direction, so as to prevent side lobes as much as possible, so as to obtain a better beam profile. Here, in order to simplify the structure of the switching circuit 20 and also facilitate control thereof, the number of sub array shape pattern may be limited to approximately 4, for example. In this case, the sub array shape patterns shown in FIGS. 5 (a), (b), (c) (or (d)), and (e) (or (f)) can be adopted.

Figure 6:
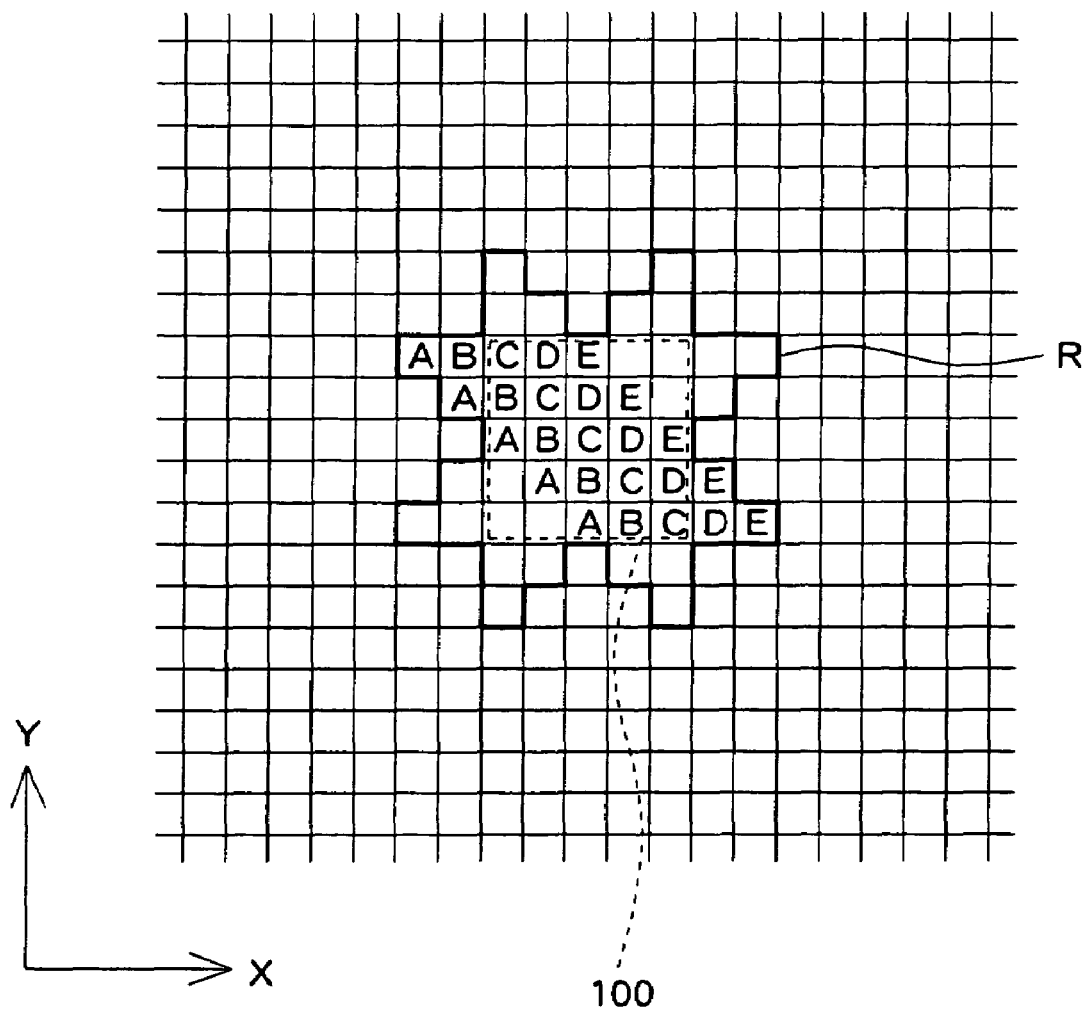
FIG. 6 is a view showing a variable range existing for each sub array.

In FIG. 6, a variable region R regarding one specific sub array is indicated with a bold line. This variable region is defined by the largest outer edge of a region which the certain sub array can have when the sub array shape changes. Therefore, the variable region R corresponds to a region obtained by superposing the shapes shown in FIGS. 5(a) to (f). In FIG. 6, numeral 100 indicates the most basic sub array shape, which is a square. Further, the grouping pattern shown in FIG. 5(c) is used, for reference, in the example of FIG. 6.

As can be understood from the shape of the variable region R shown in FIG. 6, a plurality of adjacent variable regions R partially overlap with each other. At each transmitting and receiving process, however, adjacent sub arrays are closely coupled with each other and do not overlap with each other. Overlapping of the variable regions will be described with reference to FIG. 7.

Figure 7:
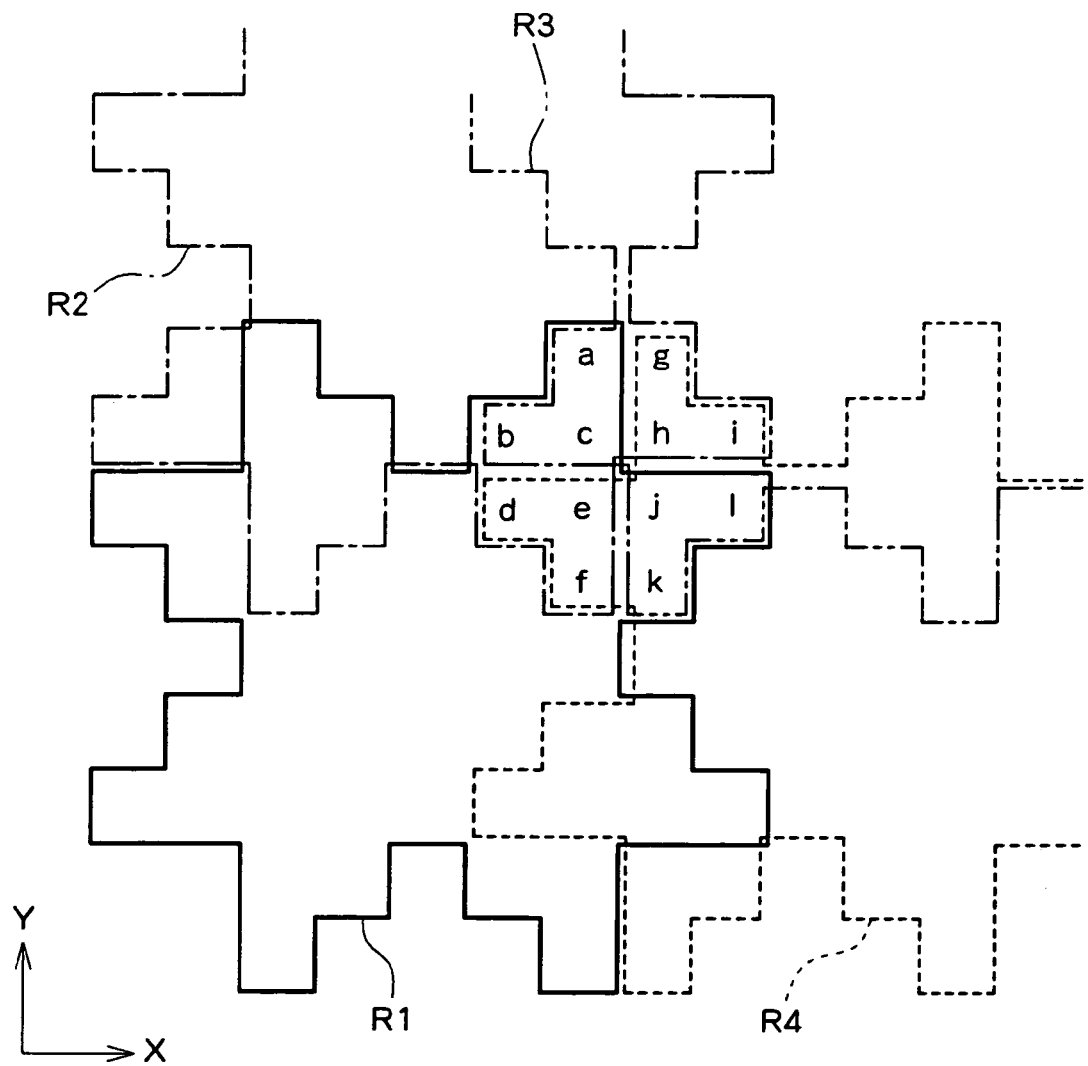
FIG. 7 is a view for explaining overlapping among a plurality of variable regions.

Referring to FIG. 7, R1 to R4 show 4 variable regions concerning 4 sub arrays, respectively, arranged adjacently in the upper-lower and right-left directions. Here, the variable region R1 is indicated by a solid line, the variable region R2 is indicated by an alternate long-and-short dashed line, the variable region R3 is indicated by an alternate long-and-two short dashed line, and the variable range R4 is indicated by a broken line.

The transducer elements a to l located in the portion where these variable regions partially overlap with each other will be explained. The transducer elements a, b, and c belong to the variable regions R1, R2, and R3, the transducer elements d, e, and f belong to the variable regions R1, R2, and R4, the transducer elements g, h, and i belong to the variable regions R2, R3, and R4, and the transducer elements j, k, and l belong to the variable regions R1, R3, and R4.

Focusing on the variable region R1, the transducer elements a to f and j to l are included within the variable region R1 (whereas the transducer elements g to i are not included), and the variable region R1 also includes a plurality of transducer elements peculiar to the variable region R1. These peculiar transducer elements include 13 transducer elements, which are disposed close to each other in a diamond shape about the center of the variable region R1.

Figure 8:
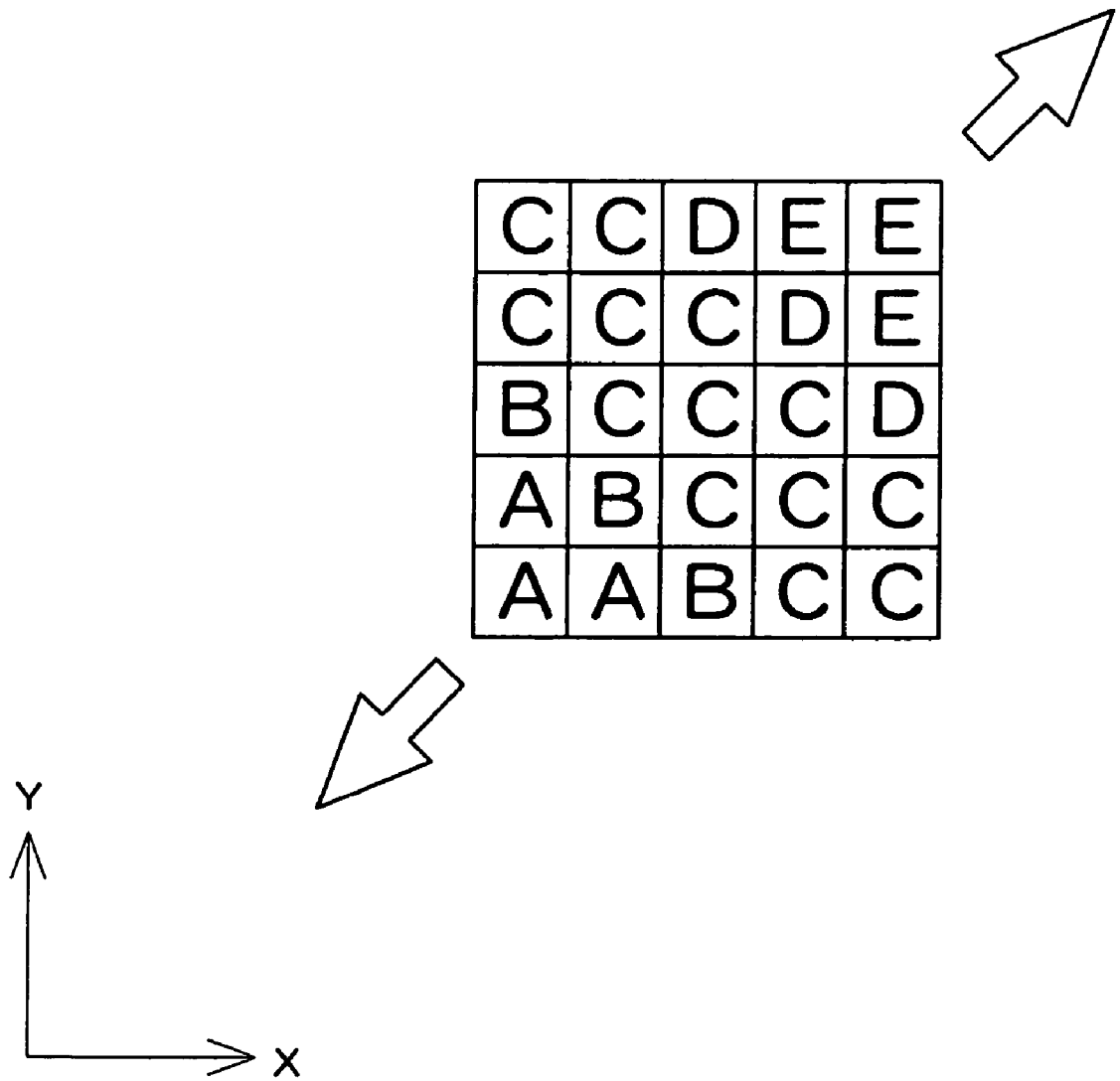
FIG. 8 is a view for explaining a comparative example.

FIG. 8 shows a comparative example. In this example, the sub array has a fixed square shape. The grouping pattern as shown in FIG. 8, for example, is set when scanning an ultrasonic beam in the diagonal direction. In this case, a plurality of transducer elements belonging to the group C exist multiply along the beam scanning direction (that is, the thickness of the transducer portion C is increased in that direction), which results in deformation of ultrasonic beam profile, causing side lobes to generate easily. According to the present embodiment, on the other hand, because it is possible to set the sub array shape and grouping pattern as shown in FIG. 4, a problem which is caused in the case as shown in FIG. 8 can be solved or reduced.

Figure 9:
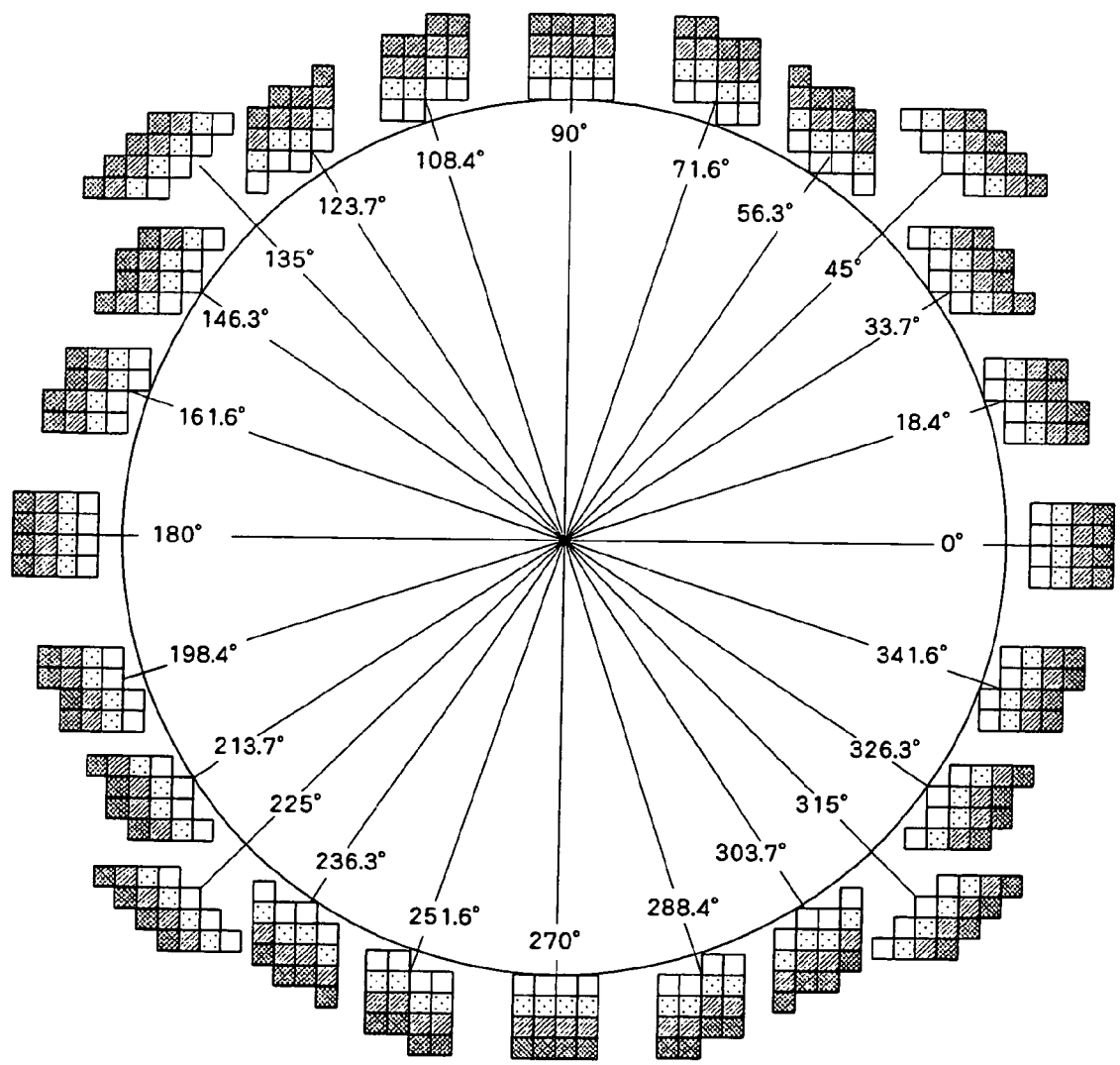
FIG. 9 is a view showing additional sub array shape patterns according to the present invention.

FIG. 9 shows another example concerning the sub array shape, in which one sub array is composed of 4×4=16 transducer elements. As shown in FIG. 9, 16 transducer elements forming each sub array are grouped into 4 groups. In FIG. 9, each group is hatched in a different manner for the purpose of identification. The numerical values shown in FIG. 9 indicate the angles represented by the scanning direction of an ultrasonic beam (the scanning azimuth).

By adaptively changing each sub array pattern (and the grouping pattern simultaneously) in accordance with the scanning direction of an ultrasonic beam as shown in FIG. 9, a preferable beam profile can be obtained in any beam direction. A plurality of sub arrays can be closely coupled with each other whichever sub array shape pattern shown in FIG. 9 is adopted. When the scanning direction is 45 degrees, for example, a plurality of sub arrays are closely coupled to each other without any interval therebetween, as shown in FIG. 4. With regard to other scanning angles, a plurality of sub arrays are similarly coupled closely with each other.

At an end portion of a 2D array transducer, however, one or a plurality of transducer elements which do not function substantially may exist. Further, while no interval is formed between a plurality of sub arrays in the above embodiment, it is possible to provide one or a plurality of transducer elements which do not function substantially between adjacent sub arrays.

The variable setting method of the sub array shape pattern as described above is also applicable to a 1.5D array transducer in which a plurality of transducer elements are arranged two-dimensionally, in addition to a 2D array transducer.

Figure 11:
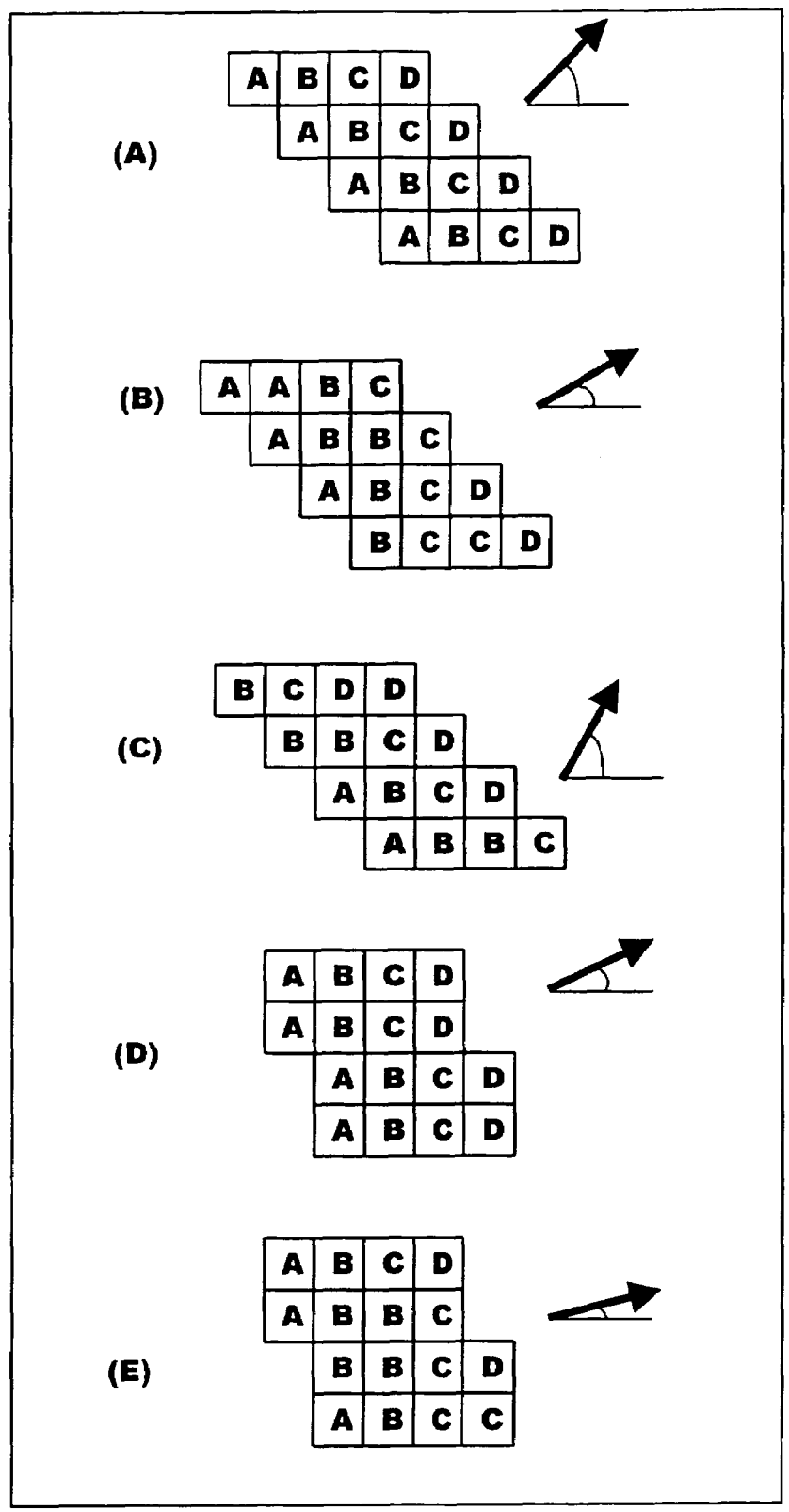
FIG. 11 is a view for explaining an embodiment in which the number of transducer elements forming each group varies.

Additional variations for changing the sub array shape pattern and the grouping pattern will be described with reference to FIGS. 11 and 12. In FIG. 11, the sub array is composed of 4×4 transducer elements.

FIG. 11(A) shows a sub array shape pattern when the beam scanning direction is 45 degrees. Each group is composed of 4 transducer elements arranged orthogonally with respect to the beam scanning direction (indicated by a bold arrow), and each group has an identical shape. FIG. 11(B) shows a sub array shape pattern when the beam scanning direction is smaller than 45 degrees. While the sub array shown in FIG. 11(B) has the same sub array shape (outer shape) as the sub array shown in FIG. 11(A), the number of transducer elements forming a group differs among a plurality of groups and the groups A, B, and C have non-linear shapes in FIG. 11(B). FIG. 11(C) shows a sub array shape pattern when the beam scanning direction is greater than 45 degrees. While the sub array shown in FIG. 11(C) has the same sub array shape as the sub array shown in FIG. 11(A), the number of transducer elements forming a group differs among a plurality of groups and the groups B, C and D have non-linear shapes in FIG. 11(C). FIG. 11(D) shows another sub array shape pattern when the beam scanning direction is smaller than 45 degrees. The sub array shown in FIG. 11(D) has a sub array shape which is different from that shown in FIG. 11(A). In FIG. 11(D), the group shape is identical for a plurality of groups. FIG. 11(E) shows a sub array shape pattern when the beam scanning direction is significantly small. While the shape of the sub array shown in FIG. 11(E) is the same as the sub array shown in FIG. 11(D), the number of transducer elements forming a group is not identical among a plurality of groups. Whichever sub array shape pattern is adopted, a plurality of sub arrays can be closely coupled with each other.

As described above, by changing both the sub array shape pattern and the group shape pattern in accordance with the beam scanning direction, a preferable ultrasonic beam can be formed. In particular, by varying the number of transducer elements forming each group in accordance with the beam scanning direction, side lobes can be reduced more effectively.

While in the above embodiment, all of a plurality of transducer elements forming each sub array function as effective transducer elements (transducer elements effecting transmission and reception of ultrasound), one or a plurality of ineffective transducer elements (transducer elements not effecting transmission and reception of ultrasound) may be provided within each sub array when the beam scanning direction corresponds to a predetermined angle. A further embodiment, configured in this manner, will be described below with reference to FIG. 12.

Figure 12:
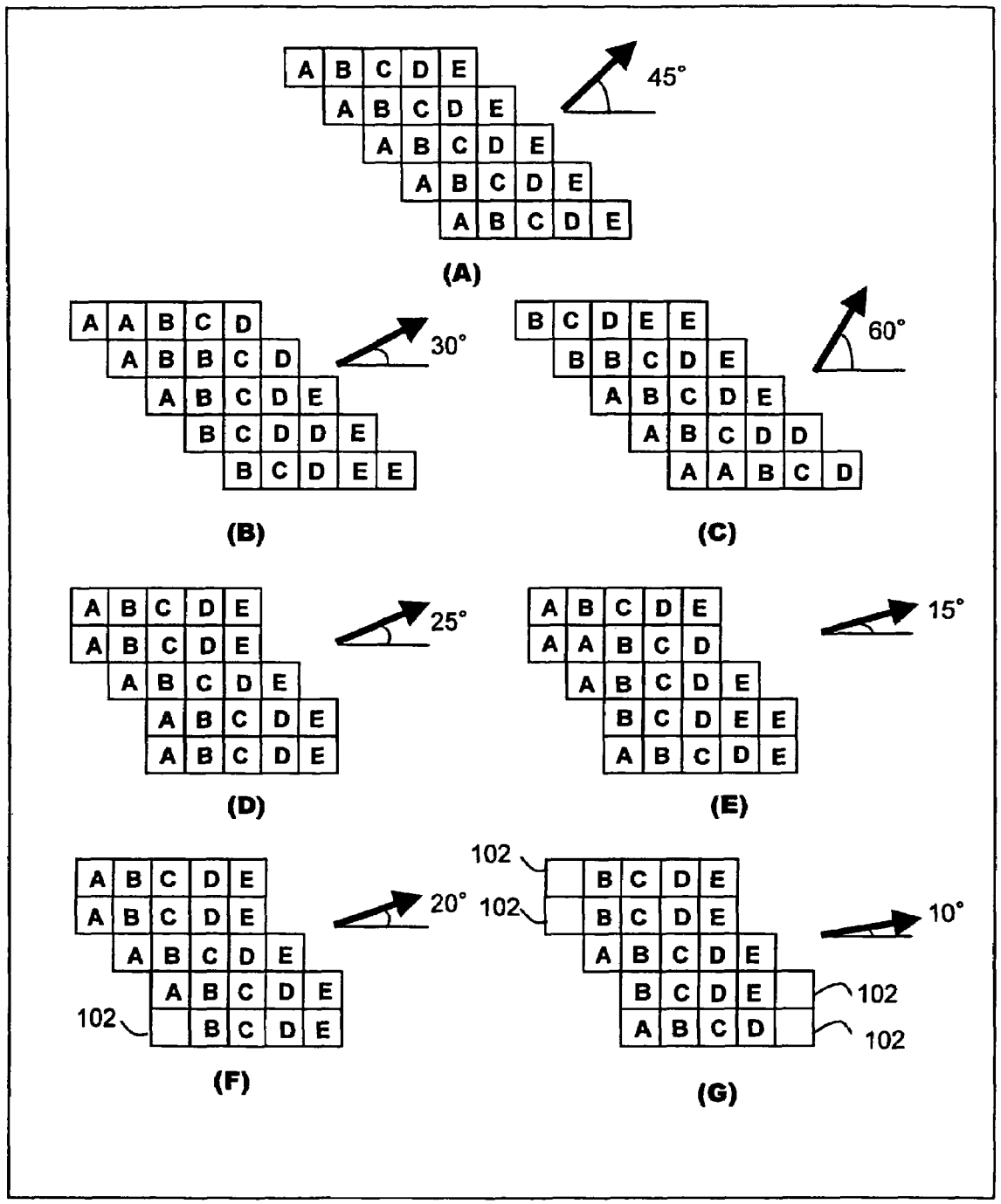
FIG. 12 is a view for explaining another embodiment of the present invention, in which the number of transducer elements forming each group varies.

In FIG. 12, the sub array is composed of 5×5 transducer elements. FIG. 12(A) shows a sub array shape pattern (which is the same as the pattern shown in FIGS. 4, 5(b), and 6) when the beam scanning direction is 45 degrees. Each group is composed of a series of transducer elements arranged orthogonally with respect to the beam scanning direction, and each series of transducer elements include 5 transducer elements. FIG. 12(B) shows a sub array shape pattern when the beam scanning direction is 30 degrees. FIG. 12(C) shows a sub array shape pattern when the beam scanning direction is 60 degrees. While the sub arrays shown in FIGS. 12(B) and (C) have the same shape as that shown in FIG. 12(A), the sub arrays shown in FIGS. 12(B) and (C) include a plurality of non-linear groups. FIG. 12(D) shows a sub array shape pattern when the beam scanning direction is 25 degrees. In FIG. 12(D), the number of transducer elements forming a group and the group shape is identical for a plurality of groups. On the other hand, FIG. 12(E) shows a sub array shape pattern when the beam scanning direction is 15 degrees. While the sub array shown in FIG. 12(E) has the same shape as the sub array shown in FIG. 12(D), these sub arrays have different grouping patterns. FIG. 12(F) shows a sub array shape pattern when the beam scanning direction is 20 degrees. While the sub array shown in FIG. 12(F) has the same shape as the sub array shown in FIG. 12(D), one ineffective transducer element 102 is included within the sub array shown in FIG. 12(F). FIG. 12(G) shows a sub array shape pattern when the beam scanning direction is 10 degrees. While the sub array shown in FIG. 12(G) has the same shape as the sub array shown in FIG. 12(E), 4 ineffective transducer elements 102 are included within the sub array shown in FIG. 12(G). In this manner, the position and the number of ineffective transducer elements are variably set in accordance with the beam scanning direction.

Whichever sub array shape pattern of those shown in FIGS. 11 and 12 is adopted, a plurality of sub arrays can be closely coupled with each other.

As described above, according to the present invention, a preferable beam profile can be obtained, which further achieves an advantage of increasing the quality of an ultrasonic image which is formed.

What is claimed is:

1. An ultrasonic diagnosis apparatus, comprising:
   a two-dimensional array transducer for forming a three-dimensional image, the two-dimensional array transducer having a plurality of transducer elements arranged two-dimensionally;
   a switching section for defining a plurality of sub arrays with respect to the plurality of transducer elements, and for defining a plurality groups for each sub-array and outputting a group receiving signal for each of the groups; and
   a receiving processing section for processing a plurality of group receiving signals output from the switching section; wherein
   the switching section changes a sub array pattern of each sub array in the array transducer in accordance with a beam forming condition, and changes a group shape pattern of each group in each of the sub arrays,
   a pattern variable region is defined for each sub array to thereby define a plurality of pattern variable regions on the array transducer,
   the pattern variable region for each sub array corresponds to a region formed by combining a plurality of sub array shape patterns concerning each sub array, and
   the plurality of pattern variable regions partially overlap with each other.

2. An ultrasonic diagnosis apparatus according to claim 1, wherein an identical sub array pattern is defined for the plurality of sub arrays.

3. An ultrasonic diagnosis apparatus according to claim 1, wherein
   the plurality of transducer elements are arranged in the X and Y direction, and
   the beam forming condition includes a beam scanning direction on a X-Y plane.

4. An ultrasonic diagnostic apparatus according to claim 1, wherein
   the number of transducer elements forming each group is variable in accordance with the beam forming condition.

5. An ultrasound diagnosis apparatus according to claim 4, wherein the beam forming condition includes a beam scanning direction.

6. An ultrasonic diagnostic apparatus according to claim 1, wherein
   one or a plurality of ineffective transducer elements are included in each sub array in accordance with the beam forming condition.

7. An ultrasound diagnosis apparatus according to claim 1, wherein
   the plurality of sub arrays are closely coupled with each other even when the sub array shape pattern is changed.

8. An ultrasonic diagnostic apparatus according to claim 1, wherein
   each pattern variable region covers a plurality of transducer elements peculiar to each sub array and a plurality of transducer elements existing on a portion where the plurality of pattern variable regions partially overlap.

9. An ultrasound diagnosis apparatus according to claim 1, wherein
   the receiving processing section includes:
   a plurality of sub phase adjusting and summing circuits, each sub phase adjusting and summing circuit performing a sub phase adjusting and summing process with respect to a plurality of group receiving signals output from each sub array and outputting a sub phase adjusted and summed signal; and
   a main phase adjusting and summing circuit for performing a main phase adjusting and summing process with respect to a plurality of sub phase adjusted and summed signals output from the plurality of sub phase adjusting and summing circuits.

10. An ultrasound diagnosis apparatus according to claim 1, wherein
    at least the array transducer and the switching section are provided within a probe head.

11. An ultrasound diagnosis apparatus according to claim 1, wherein
    each sub array shape pattern is formed by a plurality of pattern elements, and
    each of the plurality of pattern elements is formed by a series of transducer elements arranged in a substantially linear shape.

12. An ultrasonic diagnostic apparatus according to claim 11, wherein
    each series of transducer elements is substantially orthogonal with respect to a beam scanning direction as the beam forming condition.

13. An ultrasonic diagnostic apparatus according to claim 1, wherein
    each sub array has a quadrangle shape when the beam scanning direction as the beam forming direction is 0 degrees, 90 degrees, 180 degrees, and 270 degrees, and
    the shape of each sub array is changed from the quadrangle shape to a parallelogram when the beam scanning direction is an angle other than the above described angles.

* * * * *